(12) United States Patent
Muller

(10) Patent No.: US 9,872,532 B2
(45) Date of Patent: Jan. 23, 2018

(54) SWEAT MANAGEMENT PAD FOR PROTECTIVE HELMETS

(71) Applicant: Bell Sports, Inc., Scotts Valley, CA (US)

(72) Inventor: Hilgard N. Muller, Felton, CA (US)

(73) Assignee: Bell Sports, Inc., Scotts valley, CA (US)

( * ) Notice: Subject to any disclaimer, the term of this patent is extended or adjusted under 35 U.S.C. 154(b) by 0 days.

(21) Appl. No.: 15/395,077

(22) Filed: Dec. 30, 2016

(65) Prior Publication Data

US 2017/0273389 A1 Sep. 28, 2017

Related U.S. Application Data

(60) Provisional application No. 62/312,986, filed on Mar. 24, 2016.

(51) Int. Cl.
| | |
|---|---|
| *A42B 3/12* | (2006.01) |
| *A61F 13/15* | (2006.01) |
| *A42B 3/06* | (2006.01) |
| *A42B 3/28* | (2006.01) |
| *A63B 71/10* | (2006.01) |
| *A42B 3/08* | (2006.01) |

(52) U.S. Cl.
CPC .............. *A42B 3/127* (2013.01); *A42B 3/063* (2013.01); *A42B 3/066* (2013.01); *A42B 3/08* (2013.01); *A42B 3/283* (2013.01); *A61F 13/15203* (2013.01); *A63B 71/10* (2013.01)

(58) Field of Classification Search
CPC ..... A63F 13/15203; A63B 71/10; A42B 3/08; A42B 3/066; A42B 3/283; A42B 3/063; A42B 3/127

USPC ............................................................ 2/411
See application file for complete search history.

(56) References Cited

U.S. PATENT DOCUMENTS

| | | | | |
|---|---|---|---|---|
| 3,946,441 A | * | 3/1976 | Johnson .................. | A42B 3/063 2/412 |
| 5,014,365 A | * | 5/1991 | Schulz ................... | A42B 3/122 2/412 |
| 5,025,504 A | * | 6/1991 | Benston ................... | A42C 5/02 2/181.4 |
| 5,035,009 A | * | 7/1991 | Wingo, Jr. ............. | A42B 3/121 2/414 |

(Continued)

FOREIGN PATENT DOCUMENTS

JP 2000355818 12/2000

*Primary Examiner* — Shaun R Hurley
*Assistant Examiner* — Bao-Thieu L Nguyen
(74) *Attorney, Agent, or Firm* — Booth Udall Fuller, PLC

(57) ABSTRACT

A protective helmet may include an energy management material inside an outer surface, a rim positioned on an outwardly facing surface between an inner surface and the outer surface, a sweat management pad assembly with an absorbent forehead pad positioned in a front portion of the helmet proximate the rim, the assembly including at least one absorbent extension tab extending from the absorbent forehead pad and across a portion of a surface of the rim outward of the inner surface of the energy management material, wherein the absorbent extension tab extends at least half a distance across the rim between the inner surface and the outer surface, and a fastener positioned between the absorbent extension tab and the rim and coupling the absorbent extension tab to the rim.

20 Claims, 6 Drawing Sheets

(56) References Cited

U.S. PATENT DOCUMENTS

| | | | | |
|---|---|---|---|---|
| 5,058,210 | A | 10/1991 | Tivis | |
| 5,088,130 | A * | 2/1992 | Chiarella | A42B 3/066 2/411 |
| 5,324,460 | A * | 6/1994 | Briggs | A42C 2/007 2/411 |
| 5,655,227 | A * | 8/1997 | Sundberg | A42C 2/007 2/414 |
| 5,887,284 | A * | 3/1999 | Simmons | A42C 5/02 2/181 |
| 5,915,537 | A * | 6/1999 | Dallas | A42B 3/08 2/410 |
| 6,085,357 | A * | 7/2000 | Broersma | A42B 3/08 2/416 |
| 6,154,889 | A * | 12/2000 | Moore, III | A42B 3/324 2/411 |
| 6,317,896 | B1 * | 11/2001 | Timms | A42B 3/08 2/411 |
| 6,751,808 | B2 * | 6/2004 | Puchalski | A42B 3/324 2/411 |
| 6,880,176 | B2 * | 4/2005 | Timms | A42B 3/08 2/171.3 |
| 6,983,488 | B2 * | 1/2006 | Foote | A42B 3/003 2/10 |
| 7,966,673 | B1 * | 6/2011 | Gibson | A42B 1/08 2/410 |
| 8,112,821 | B1 * | 2/2012 | Barry | A42C 5/02 2/181 |
| 8,997,265 | B2 * | 4/2015 | Olivares Velasco | A42B 3/125 2/171.1 |
| 2002/0002730 | A1 * | 1/2002 | Dennis | A42B 3/12 2/411 |
| 2004/0163162 | A1 * | 8/2004 | Benziger | A42B 1/08 2/411 |
| 2005/0268382 | A1 * | 12/2005 | Epling | A42C 5/04 2/411 |
| 2007/0056081 | A1 * | 3/2007 | Aspray | A42B 3/046 2/411 |
| 2008/0263751 | A1 | 10/2008 | Flatt | |
| 2011/0307997 | A1 * | 12/2011 | Blair | A42B 1/08 2/414 |
| 2012/0260406 | A1 * | 10/2012 | Green | A42C 5/02 2/411 |
| 2012/0297526 | A1 * | 11/2012 | Leon | A42B 3/12 2/413 |
| 2013/0232667 | A1 * | 9/2013 | Leon | A42B 3/12 2/411 |
| 2014/0196198 | A1 * | 7/2014 | Cohen | F41H 1/04 2/414 |
| 2015/0216249 | A1 * | 8/2015 | Leon | A42B 3/12 2/412 |
| 2015/0264993 | A1 * | 9/2015 | Vito | A42B 3/125 2/414 |
| 2015/0327618 | A1 * | 11/2015 | Leon | A42B 3/12 2/413 |
| 2015/0327619 | A1 * | 11/2015 | Leon | A42B 3/12 2/413 |
| 2016/0095375 | A1 * | 4/2016 | Ho | A42B 3/128 2/411 |

* cited by examiner

000# SWEAT MANAGEMENT PAD FOR PROTECTIVE HELMETS

CROSS REFERENCE TO RELATED APPLICATION

This application claims the benefit of the filing date of U.S. Provisional Patent Application No. 62/312,986, entitled "Sweat management pad for Protective Helmets" and filed on Mar. 24, 2016, the disclosure of which being hereby incorporated entirely herein by reference.

TECHNICAL FIELD

This disclosure relates to a sweat management pad system for a helmet, and more particularly to a helmet sweat management pad system with a sweat extension tab that extends forward beneath the front brim of the helmet.

BACKGROUND

Protective headgear and helmets have been used in a wide variety of applications and across a number of industries including sports, athletics, construction, mining, military defense, and others, to prevent damage to a user's head and brain. Damage and injury to a user can be prevented or reduced by helmets that prevent hard objects or sharp objects from directly contacting the user's head. Damage and injury to a user can also be prevented or reduced by helmets that absorb, distribute, or otherwise manage energy of an impact.

For helmet-wearing athletes in many applications, such as sports, beyond the safety aspects of the protective helmet, additional considerations can include comfort of the helmet during vigorous activity. Many athletes generate significant perspiration under the helmet, and this sweat may run or drip into the athlete's eyes or onto protective eyewear. Depending on the sport, impaired vision or impaired focus due to dripping sweat may create a risk of injury or hinder the athlete's performance. Improvements in sweat management in a helmet can reduce distractions to the athlete and thereby improve safety and performance.

SUMMARY

According to an aspect of the disclosure, a protective helmet may comprise an outer surface, an energy management material positioned within the outer surface and an inner surface facing away from the outer surface, a rim positioned on an outwardly facing surface between the inner surface and the outer surface of the energy management material, an adjustable fit system coupled to the energy management material inside the outer surface, a sweat management pad assembly coupled to the fit system having an absorbent forehead pad positioned in a front portion of the helmet proximate the rim, and at least one absorbent extension tab extending from the absorbent forehead pad and across a portion of a surface of the rim outward of the inner surface of the energy management material, wherein the absorbent extension tab extends at least half a distance across the rim between the inner surface and the outer surface, and a fastener positioned between the absorbent extension tab and the rim and coupling the absorbent extension tab to the rim.

Particular embodiments may comprise one or more of the following features. The absorbent forehead pad and the absorbent extension tab may be commonly constructed. The absorbent extension tab may couple to the rim at the front portion of the helmet positioned above a nose of the wearer of the helmet. The at least one absorbent extension tab may be positioned on the surface of the rim symmetrically about a center-line of the front portion of the helmet. The absorbent extension tab comprises a moisture wicking material adapted to draw moisture away from the forehead pad to the absorbent extension tab.

According to an aspect of the disclosure, a protective helmet may comprise an energy management material comprising an outer surface and an inner surface facing away from the outer surface, a rim positioned between the inner surface and the outer surface, an adjustable fit system coupled to the energy management material and positioned inside the helmet, a pad assembly coupled to the fit system having an absorbent forehead pad positioned in a front portion of the helmet proximate the rim, and at least one absorbent extension tab extending from the forehead pad and across a portion of a surface of the rim outward of the inner surface of the energy management material.

Particular embodiments may comprise one or more of the following features. A fastener positioned between the at least one absorbent extension tab and the rim and coupling the absorbent extension tab to the rim. The at least one absorbent extension tab may extend across more than half a distance of the rim between the inner surface and the outer surface. The at least one absorbent extension tab may extend across at least ¾ of the distance across the rim between the inner surface and the outer surface. The at least one absorbent extension tab may couple to the rim at the front portion of the helmet positioned above a nose of the wearer of the helmet. The at least one absorbent extension tab may couples to the rim at a front half of the helmet. The forehead pad and each of the at least one absorbent extension tab may comprise a common, continuous absorptive material. The at least one absorbent extension tab may be positioned on the surface of the rim symmetrically about a center-line of the front portion of the helmet.

According to an aspect of the disclosure, a protective helmet may comprise a shell assembly comprising an outer surface and an inner surface facing away from the outer surface, a rim positioned between the inner surface and the outer surface of the shell assembly, a pad assembly coupled to the helmet inside of the shell assembly having an absorbent forehead pad positioned in a front portion of the helmet proximate the rim, and at least one absorbent extension tab coupled to the forehead pad and extending across a portion of a surface of the rim outward of the inner surface of the shell assembly.

Particular embodiments may comprise one or more of the following features. A fastener positioned between the absorbent extension tab and the rim and coupling the absorbent extension tab to the rim. An outer shell, wherein the outer surface of the shell assembly is an outer surface of the outer shell, and an energy management material positioned within the outer shell, wherein the inner surface of the shell assembly is an inner surface of the energy management material facing away from the outer shell. The at least one absorbent extension tab extends across at least ¾ of a distance across the rim between the inner surface and the outer surface, and wherein the at least one absorbent extension tab couples to the rim at the front portion of the helmet positioned symmetrically about a center of the helmet. A recess in the surface of the rim, wherein the fastener couples the absorbent extension tab to the rim at the recess. The absorbent extension tab may not protrude beyond the depth of the recess for more than half of a height of the absorbent extension tab. A plurality of channels on a surface of the absorbent extension tab and extending outward from the forehead pad.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. §112, ¶ 6. Thus, the use of the words "function," "means" or "step" in the Detailed Description or Description of the Drawings or claims is not intended to somehow indicate a desire to invoke the special provisions of 35 U.S.C. §112, ¶ 6, to define the invention. To the contrary, if the provisions of 35 U.S.C. §112, ¶ 6 are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶ 6. Moreover, even if the provisions of 35 U.S.C. §112, ¶ 6 are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Illustrative and exemplary embodiments of the disclosure are shown in the drawings in which.

Figure 1:
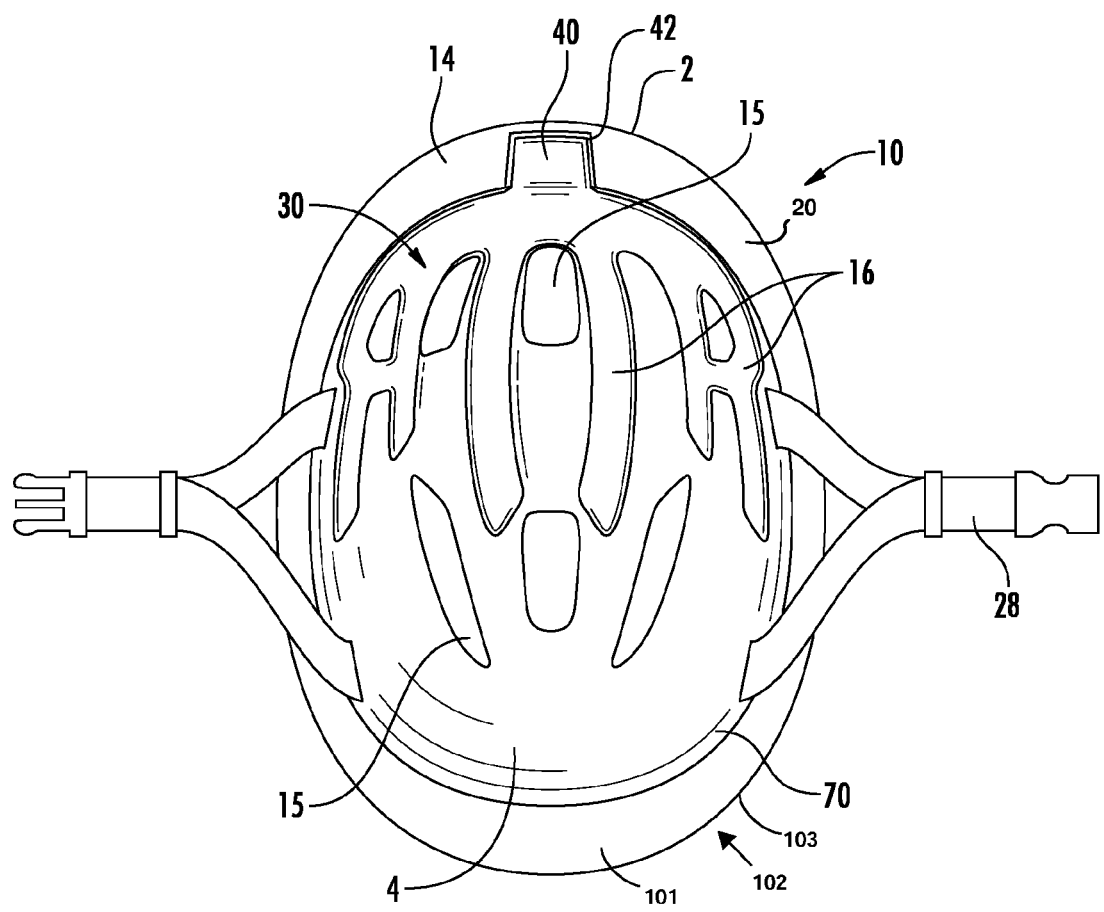
FIG. 1 is a plan view of an underside of a protective helmet with a sweat management pad.

Elements and facts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the disclosure. It will be understood, however, by those skilled in the relevant arts, that the present disclosure may be practiced without these specific details. In other instances, known structures and devices are shown or discussed more generally in order to avoid obscuring the disclosure. In many cases, a description of the operation is sufficient to enable one to implement the various forms of the disclosure. It should be noted that there are many different and alternative configurations, devices and technologies to which the disclosure may be applied. The full scope of the disclosure is not limited to the examples that are described below.

Accordingly, this disclosure describes protective headgear, as well as a system and method for providing a helmet or protective headgear, that can be used for a cyclist, mountain biker, football player, hockey player, baseball player, lacrosse player, polo player, climber, auto racer, motorcycle rider, motocross racer, skier, snowboarder or other snow or water athlete, sky diver, mountaineer, rock climber or any other athlete, whether recreational or professional, that engages in a sport using protective headgear. Other non-athlete users such as workers involved in industry, including without limitation construction workers or other workers or persons in dangerous work environments can also benefit from the protective headgear described herein, as well as the system and method for providing the protective headgear. Each of the above listed sports, occupations, or activities can use a protective headgear (e.g., a protective helmet) that includes an either single or multi-impact rated protective material base that is typically, though not always, covered on the outside by a decorative cover and/or hard-shell, and includes comfort material on at least portions of the inside, usually in the form of comfort padding.

Various implementations and embodiments of protective headgear and protective helmets according to this disclosure comprise a protective shell. The protective shell can be made of an energy management material, such as expanded polystyrene (EPS), expanded polyurethane (EPU), expanded polyolefin (EPO), expanded polypropylene (EPP), or other suitable material. The energy management material functions to absorb and/or dissipate the energy resulting impacts that may otherwise injure the wearer, and may operate as a single-impact rated (e.g., many types of cycling helmets) or multi-impact rated (e.g., typical hockey helmets) energy management material. The energy management material may also be referred to as an energy absorbing material. The energy management material can be part of a hard-shell helmet such as a skate bucket helmets, motorcycle helmets, snow sport helmets, football helmets, batting helmets, catcher's helmets, or hockey helmets, and include an additional outer protective shell disposed outside, or over, the protective shell. In hard shell applications, the energy management material can comprise one or more layers of EPP and provide more flexibility than available with conventional in-molded helmets. Alternatively, the energy management material can be part of an in-molded helmet such as a cycling helmet. As an energy-absorbing layer in an in-molded helmet, the protective shell can comprise rigid materials such as EPS and EPU. An outer shell layer, such as a layer of stamped polyethylene terephthalate (PET) or a polycarbonate shell, can be included on an outer surface of the protective shell of the helmet and be bonded directly to the expanding foam (e.g., EPS as it is expanding such that the foam is molded in the shell). The protective shell may or may not have air vents 15 (FIG. 1) extending through one or more layers of energy management material to allow for cooling and moisture removing air flow through portions of the helmet.

Various embodiments of a protective helmet of this disclosure further comprise a sweat management pad. Unless otherwise specified, a sweat management pad according to this disclosure may comprise any material, padding, and configuration of inner pads previously known in the art, including an inner pad system comprising a single pad or a plurality of inner pads. In a non-limiting embodiment, the sweat management pad comprises a compression open molded, open cell foam laminated with a technical fabric adapted to absorb sweat. In other embodiments, the material may comprise any material adapted to channel moisture to a specific location and/or through the material. In one or more embodiments, a sweat management pad comprises at least one extension tab. The extension tab extends from the body of the sweat management pad such that when the sweat management pad is coupled to or positioned proximate an inner surface of the protective shell, the extension tab extends outward from body of the inner pad towards the outer surface of the protective helmet.

Comfort pads of a conventional helmet are positioned inside the helmet at the wearer's forehead and sometimes extend up along the inside surface of the helmet toward the top of the wearer's head. As a result, when the wearer sweats, the sweat is absorbed by the comfort pads and the sweat, affected by gravity, starts to collect in the lowest points on the comfort pads, which is inside the helmet above the wearer's eyes. When saturation is reached or enough sweat has collected, the sweat begins to drip down, draining along the wearer's forehead into the wearer's eyes, or dripping on the wearer's face. This is a distraction to the wearer.

FIG. 1 is an underside view of a non-limiting embodiment of a sweat management pad or inner pad 30 coupled to a protective helmet 10. The helmet 10 may be any protective helmet known in the art. For the particular embodiment illustrated in FIG. 1, the helmet 10 is a cycling helmet with air vent apertures 15 extending through the helmet from the outer shell 103, having an outer surface 2, to the inner surface 4. A shell assembly 102 may be formed of one or more layers of energy management materials 101 and may include a hard outer shell 103 with one or more softer energy management materials therein, a soft outer shell 103 with one or more energy management materials therein, or simply one or more energy management materials (also see FIGS. 2-4). If only an energy management material layer is used, that layer forms the shell assembly. A sweat management pad 30, comprising a plurality of fingers 16 extending toward the rear end of the helmet 10 is coupled to the inner surface 4 of the helmet 10, which may include being coupled to the inner surface of a fit system 70 mounted within the helmet. The use of fit systems in helmets to allow a user to adapt the fit system to fit the user's head for more secure helmet attachment to the user's head is known in the art and any fit system known in the art may be used in combination with the sweat management pad and extension tab 40 disclosed herein. Though not required, the particular helmet embodiment illustrated in FIGS. 1, 2 and 4 includes a recess 42 at the point on the rim 14 of the helmet 10 where the extension tab 40 extends forward of the sweat management pad between the inner surface 4 and the outer surface 2 of the helmet 10.

Figure 2:
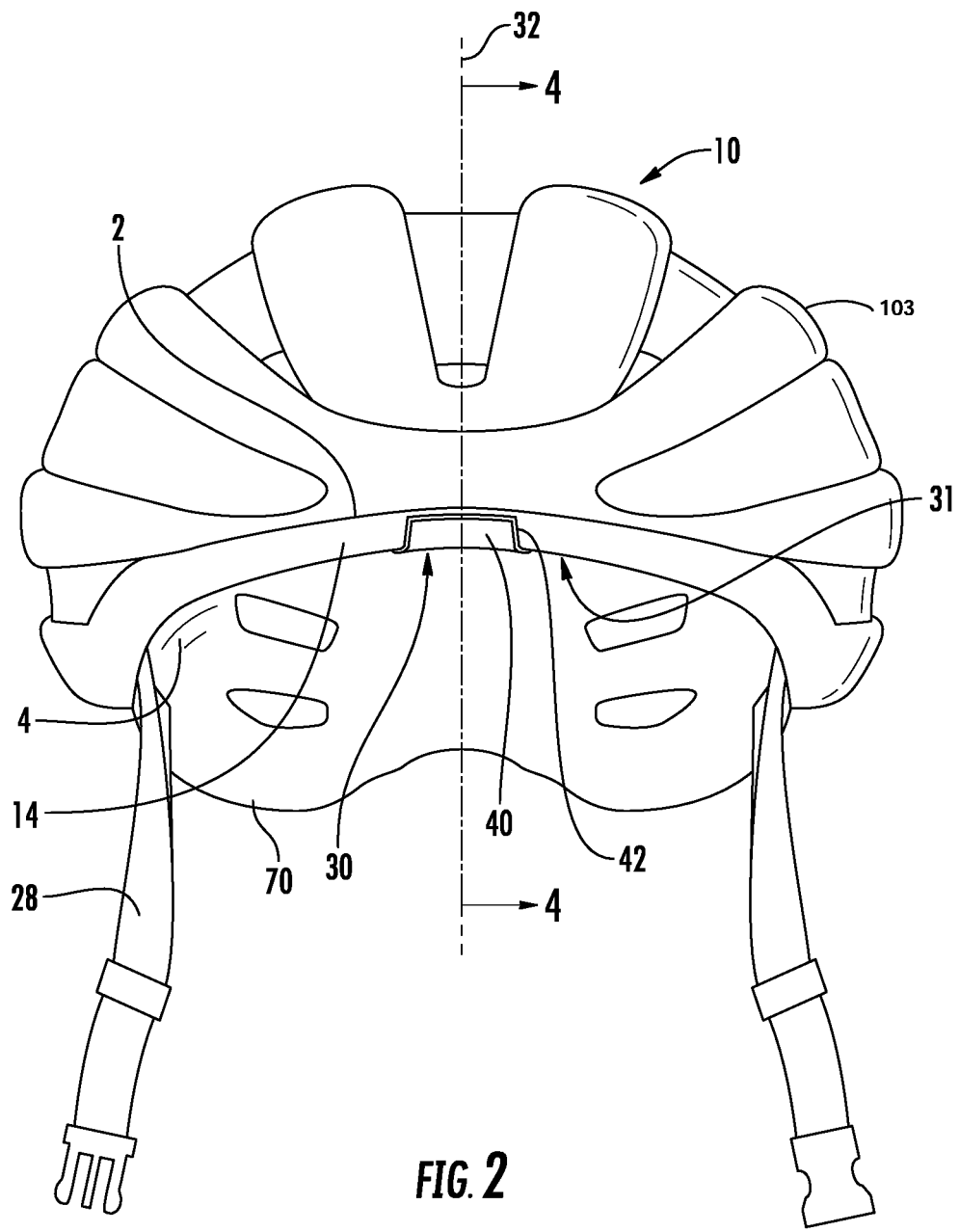
FIG. 2 is a front view of the protective helmet of FIG. 1.

FIG. 2 is a front view of a non-limiting embodiment of a sweat management pad 30 coupled to a protective helmet 10. The front view illustrates the extension tab 40 extending forward of the inner surface 4 of the helmet 10 toward the outer surface 2 of the helmet across the underside 31 of the helmet 10 rim 14. Although it is not a requirement of this disclosure, particular embodiments of a sweat management pad 30 may comprise one or more extension tabs 40 symmetrically positioned about the center 32 of the helmet 10. FIG. 2 illustrates a single extension tab 40 symmetrically positioned about the center 32 of the helmet. Other embodiments may comprise multiple extension tabs positioned symmetrically on opposing sides of the center 32 of the helmet instead of or in addition to the position of the extension tab 40 illustrated in FIG. 2.

Figure 3:
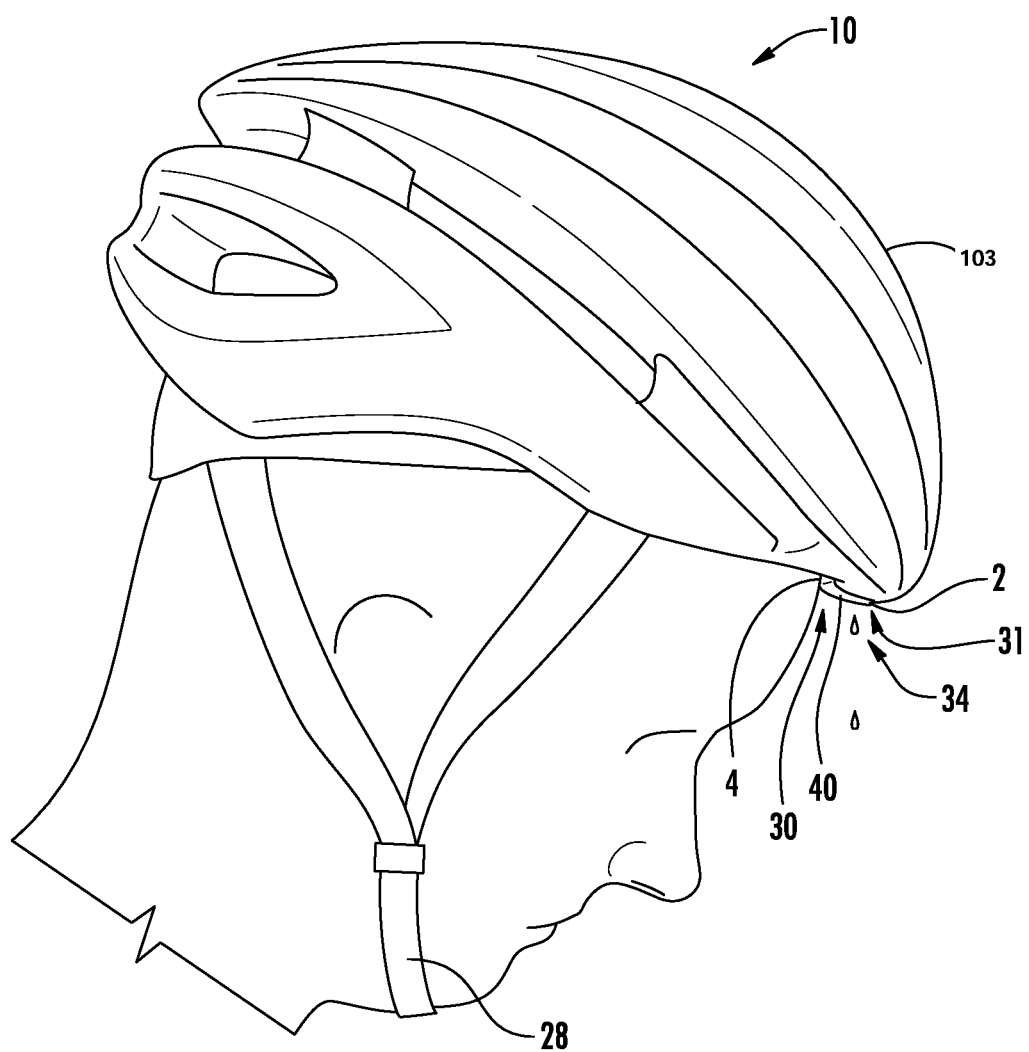
FIG. 3 is a side view of a protective helmet and sweat management pad shown worn by a wearer.

FIG. 3 is a side view of a protective helmet 10 with a sweat management pad 30 on the head of a user to illustrate the sweat dripping 34 from the sweat management head. When a cyclist rides a bicycle, often the cyclist tilts his head forward for comfort and mechanical advantage when riding. As a result, the sweat that typically collects on the sweat management pad 30 collects through the continuous sweat management pad 30 out to the extension tab 40 because it is the lowest point on the sweat management pad 30. When the wearer's head is tilted forward as in FIG. 3, the sweat drips 34 from the extension tab 40 and does not drip into the rider's face. The sweat management pads 30 illustrated in the various embodiments comprise at least one extension tab 40 extending forward of the rest of the sweat management pad 30 and coupled to an underside 31 of the front rim 14 of the helmet.

In particular embodiments, the helmet may comprise an extension tab receiver 12 on the underside of the rim, sized to receive the extension tab 40 of the sweat management pad 30 with the extension tab 40 positioned within the extension tab receiver 12. In some embodiments, the extension tab receiver 12 may be recessed a certain depth 13 below the surface 20 of the rim 14. For example, the extension tab receiver 12 may be recessed such that when the extension tab 40 is positioned within the recess of the extension tab receiver 12, the extension tab 40 is flush with the rim 14 of the helmet 10 and does not protrude into the rider's normal line of sight. In alternative embodiments, the extension tab receiver 12 is not recessed such that the extension tab receiver 12 is flush with the rim surface 20. In more particular embodiments, the extension tab receiver 12 and the extension tab 40 may comprise couplings 50 configured to allow a user to removably couple the extension tab 40 to the extension tab receiver 12. The couplings 50 may comprise any couplings adapted to allow a user to removably couple the extension tab 40, such as but not limited to snap buttons, hook and look fasteners, magnets, adhesives, and the like. In other embodiments, a rim 14 of a helmet 10 may comprise a coupling 50 configured to removably couple to the extension tab 40 without an extension tab receiver 12. In an event, the extension tab 40 and the protective helmet 10 are configured such that when the extension tab 40 is coupled to the rim 14 of the helmet 10, the extension tab 40 is angled away from the inner surface 4 of the helmet 10. The extension tab 40 may be coupled to the rim 14 of the helmet 10 using adhesive or other releasable coupler such as hook-and-loop fasteners.

The sweat management pad 30 includes at least one extension tab 40. In some embodiments, the sweat management pad 30 includes two or more extension tabs 40 (e.g., 2, 3, 4, 5, or any number of multiple extension tabs 40). In certain embodiments, a first version of a sweat management pad 30 has numerous small extension tabs 40 (e.g., 10 extension tabs 40) that drain about the same amount of sweat as a second version of a sweat management pad 30 that has fewer but larger extension tabs 40 (e.g., 1-3 extension tabs 40). FIG. 2 illustrates a non-limiting embodiment where sweat management pad 30 includes only one extension tab 40 and the main body of the sweat management pad 30 includes a forehead pad 45 adapted to rest or press against at least part of the forehead or frontal brow area of the wearer when using the helmet 10. The sweat management pad 30 is not limited to being used to wick away moisture at or near the forehead, and may be extended with sweat management pad fingers 16 positioned near the sides, the back, or top of the head in some embodiments.

One or more embodiments of a protective helmet 10 may comprise a fit system 70 that couples the sweat management pad 30 to the protective helmet 10 by coupling at or proximate the inner surface 4 of the protective helmet 10. The fit system 70 may be adjustable to provide a comfortable and secure fit of the helmet 10 during use. In some embodiments, a chin strap 28 couples to at least one of the helmet 10 and fit system 70. The chin strap 28 includes a releasable snap, clasp, or other fastener so that the wearer can secure the helmet 10 to the head by fitting the chin strap 28 with a closed fastener beneath the chin of the wearer.

Figure 4:
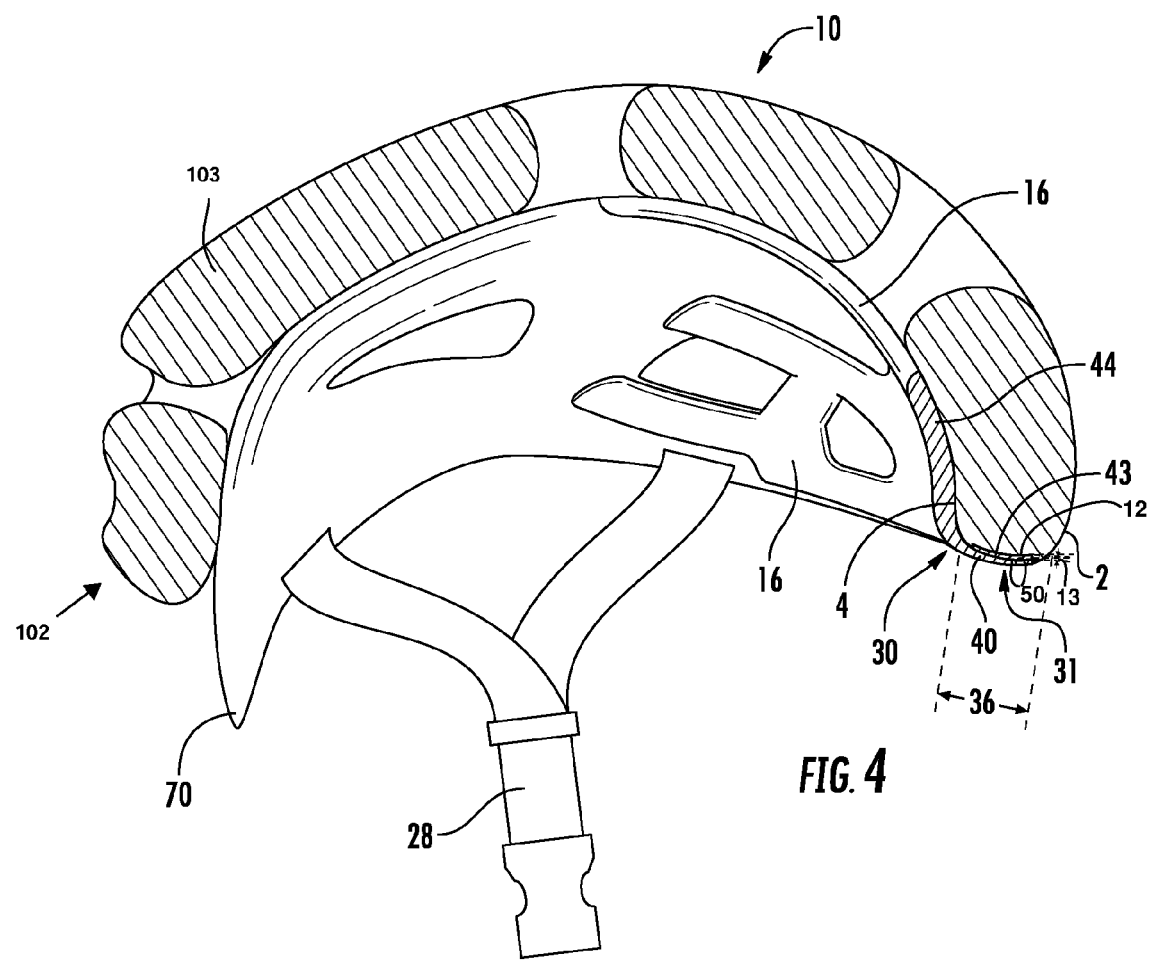
FIG. 4 is a sectional view of the protective helmet and sweat management pad of FIG. 1 taken along section line 4-4 shown in FIG. 2.

FIG. 4 is a cross-sectional view of a non-limiting embodiment of a portion of a sweat management pad 30 coupled to a protective helmet 10. As shown in FIG. 4 and referenced above, the extension tab 40 of the sweat management pad 30 is directed away from the inner surface 4 of the helmet 10 where the body of the sweat management pad 30 is positioned towards the outer surface 2 of the protective helmet 10. The width 36 of the rim 14 is the thickness measured between the inner surface 4 and the outer surface 2 of the helmet 10 at the front of the helmet, and the rim width 36 may be uniform or vary throughout the rim 14. In some embodiments, the extension tab 40 protrudes outwards by extending across the width 36 of the rim 14 from 30% to 100% of the width 36 of the rim 14. In some embodiments, the extension tab 40 extends forward across the rim at least 50% of the width of the helmet 10. In particular embodiments, a fastener 43 is positioned between the rim 14 and the extension tab 40 to couple the extension tab 40 to the rim 14 of the helmet.

Figure 5:
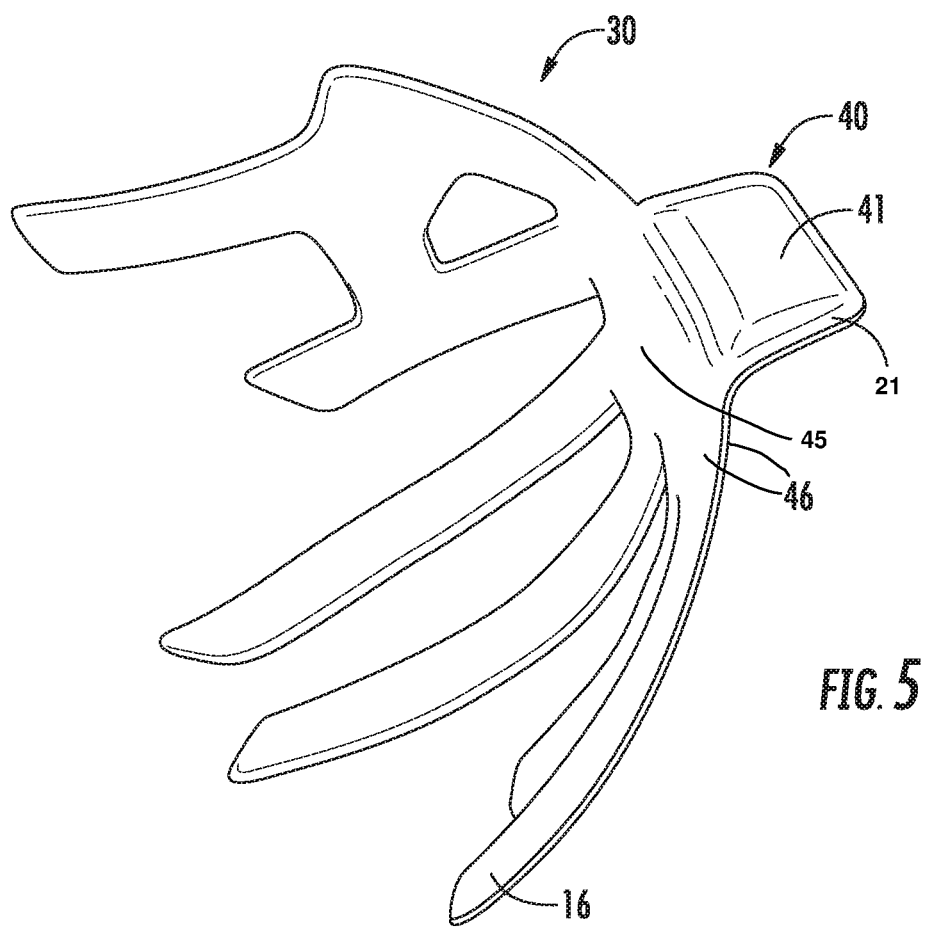
FIG. 5 is a perspective view of a sweat management pad.

As illustrated in FIG. 5, in some embodiments, the extension tab 40 is thicker than the remainder of the sweat management system 30 and includes a belly 41 or thickest portion of the extension tab 40 that is at least 25% thicker than the remainder of the sweat management system 30. The forehead pad 45 is positioned immediately between the extension tab 40 and the remainder of the sweat management pad 30.

Particular shapes of extension tabs may be used for particular applications of the technology. In some embodiments, the extension tab 40 may have a generally rectangular, square, trapezoidal, triangular, or other rectilinear shape. In certain embodiments, the extension tab 40 may have a generally curvilinear or irregular shape. In other embodiments, the extension tab 40 may have a shape of a symbol, trademark, silhouette, or alphanumeric character. In one or more embodiments, the extension tab 40 has a generally acute trapezoidal or isosceles trapezoidal shape. The extension tab 40 may be constructed to have a thick absorbent center (e.g., a belly or thickest portion) that is encircled on at least two sides by thin boundaries 21. For example, the thin boundaries may be formed with at least two different layers of the extension tab 40 being compressed by heat welding, stitching, molding, or other fastening mechanisms.

Although reference is made herein to the rim 14 of the helmet 10, it is also contemplated that in some embodiments a similarly configured and positioned extension tab 40 may be positioned at the rear edge of the helmet 10. In still other embodiments, a sweat management pad 30 may comprise one or more extension tabs 40 positioned in alternative or addition to a front or rear extension tab 40. For example, a sweat management pad 30 may comprise an extension tab 40 positioned anywhere on the helmet 10 that is not in contact with the wearer to wick moisture away from the wearer (where "wick" does not require a capillary action, but rather describes drawing, emptying, moving, absorbing, or draining away moisture with the aid of gravity, a structure of the material(s), capillary action, or any other physical or chemical method of draining or moving moisture). By way of non-limiting example, an extension tab 40 may be housed in or near a vent or channel on the protective helmet 10, such that the sweat from the wearer would be wicked into the extension tab 40 and the flow of air over the extension tab 40 proximate the vent helps dry the extension tab 40 and prevent excess build-up of sweat in the inner pad 30.

In some embodiments the main body of the sweat management pad 30 (e.g., forehead pad 45) and the extension tab 40 are constructed of similar materials, the same materials, or share a similar or same core material encased by a textile (e.g., an athletic textile) on at least one side. The sweat management pad 30 and the extension tab 40 may also be constructed of a core 44 material sandwiched between two cover 46 layers (see FIG. 4) or having a cover layer 46 at least between the core 44 and the skin of the wearer. The sweat management pad 30 and the extension tab 40 may be constructed of core 44 material sandwiched between a first cover layer and a second cover layer. The sweat management pad 30 and the extension tab 40 may be constructed with a core 44 made of one or more of: foam; open cell foams, plastics or polymers; polyurethane (PU); polyethylene (PE); dryfast foam; or other moisture permeable, wicking and/or moisture absorbent materials. The sweat management pad 30 and the extension tab 40 may be constructed using one or more cover 46 layers, such as: athletic textile; loose-knit fibers; LYCRA® fabrics; spandex; X-STATIC® materials from Noble Biomaterials, Inc. of Scranton, Pa.; COOLMAX® fabrics from Koch Industries, Inc. of Wichita, Kans.; SUPPLEX® or TACTEL® fabrics from Invista, Inc. of Wichita, Kans.; wicking fabrics from Drirelease of East Brunswick, N.J.; DRI-FIT® fabrics from Nike, Inc. of Beaverton, Oreg.; MERYL® fabrics from Nylstar, SA of Girona, Spain; or other moisture permeable, wicking and/or moisture absorbent textiles. Further, the core 44 and/or the cover 46 layer(s) may include woven natural, synthetic, or blends of natural and synthetic yarns. Still further, the core 44 and/or the cover 46 layer(s) may include one or more of various combinations of nylon, elasthan, polyester, polymid, polyurethane, thermoplastic elastomer, rubber, and latex.

Figure 6:
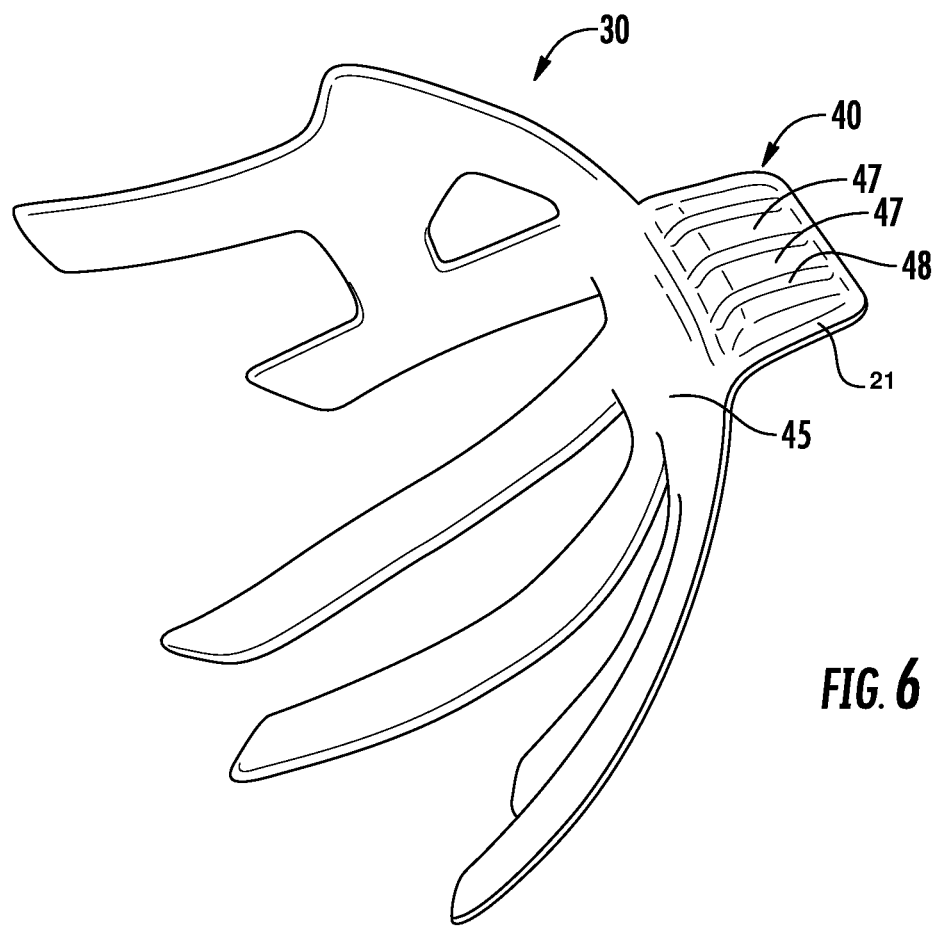
FIG. 6 is a perspective view of a sweat management pad with liquid channels.

In some embodiments, the protective helmet 10 comprises at least one sweat management pad 30, and may also comprise one or multiple separate comfort pads. The comfort pads may be formed of the same material or may differ from the construction of the sweat management pad 30 at least because the comfort pads are not operatively coupled or affixed to an extension tab 40 that transfers sweat from the comfort pad. As illustrated in FIG. 6, in other embodiments, a sweat management pad 30 may comprise channels 47 formed by sweat absorbing material separated by thinned portions 48, formed of less absorbing material, to channel sweat to particular portions of the extension tab 40. In particular embodiments, the channels may be directed away from particular parts of the face of a user so that, for example, the sweat doesn't drip directly in front of or on the user's nose, but goes to either side of the nose. This may be accomplished by extension tabs 40 that do not sit immediately above the nose of the wearer of the helmet, or through the extension tab extending above the nose of the wearer of the helmet, but including channels 47 to selectively move the sweat to drip where desired.

It will be understood that implementations are not limited to the specific components disclosed herein, as virtually any components consistent with the intended operation of a method and/or system implementation for inner pads and protective helmets may be utilized. Accordingly, for example, although particular inner pads and protective helmets may be disclosed, such components may comprise any shape, size, style, type, model, version, class, grade, measurement, concentration, material, weight, quantity, and/or the like consistent with the intended operation of a method and/or system implementation for an inner pad may be used. In places where the description above refers to particular implementations of protective helmets and inner pads, it should be readily apparent that a number of modifications may be made without departing from the spirit thereof and that these implementations may be applied to other helmets and inner pads.

Upon reading the teachings of this specification, those with ordinary skill in the art will appreciate that, under certain circumstances, considering issues such as changes in technology, user requirements, etc., a variety of fastening devices may be used to "affix", "couple", and/or "releasably couple" (as those words are used herein) one or more components of the present disclosure. These fastening devices may include one or more of the following: adhesives, bolts, buckles, clasps, latches, locks, screws, snaps, clamps, connectors, couplings, ties, or other fastening methods yet to be developed.

The concepts disclosed herein are not limited to the specific implementations shown herein. For example, it is specifically contemplated that the components included in particular implementations may be formed of any of many different types of materials or combinations that can readily be formed into shaped objects and that are consistent with the intended operation of the implementations. For example, the components may be formed of: rubbers (synthetic and/or natural) and/or other like materials; polymers and/or other like materials; plastics, and/or other like materials; composites and/or other like materials; metals and/or other like materials; alloys and/or other like materials; and/or any combination of the foregoing.

Furthermore, embodiments may be manufactured separately and then assembled together, or any or all of the components may be manufactured simultaneously and integrally joined with one another. Manufacture of these components separately or simultaneously, as understood by those of ordinary skill in the art, may involve extrusion, pultrusion, vacuum forming, injection molding, blow molding, resin transfer molding, casting, punching, and/or the like. If any of the components are manufactured separately, they may then be coupled or removably coupled with one another in any manner, such as with adhesive, a weld, a fastener, any combination thereof, and/or the like for example, depending on, among other considerations, the particular material(s) forming the components.

In places where the description above refers to particular implementations, it should be readily apparent that a number of modifications may be made without departing from the spirit thereof and that these implementations may be applied to other implementations disclosed or undisclosed. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

What is claimed is:

1. A protective helmet, comprising:
   a shell assembly comprising an outer surface and an inner surface opposite the outer surface, an energy management material positioned within the outer surface and the inner surface, and a rim positioned on an outwardly facing surface between the inner surface and the outer surface of the energy management material;
   a fit system coupled to the energy management material inside the outer surface;
   a sweat management pad assembly coupled to the fit system, the sweat management pad assembly comprising:
      a moisture absorbent forehead pad positioned in a front portion of the helmet proximate the rim;
      one or more pad fingers extending from the moisture absorbent forehead pad toward a rear end of the protective helmet; and
      at least one moisture absorbent extension tab extending from the moisture absorbent forehead pad and across a portion of a surface of the rim outward of the inner surface, wherein the moisture absorbent extension tab extends at least half a distance across the rim between the inner surface and the outer surface; and
   a fastener positioned between the moisture absorbent extension tab and the rim and coupling the moisture absorbent extension tab to the rim.

2. The protective helmet of claim 1, wherein the moisture absorbent extension tab couples to the rim at the front portion of the helmet configured to be positioned above a nose of a wearer of the helmet.

3. The protective helmet of claim 1, wherein the at least one moisture absorbent extension tab is positioned on the surface of the rim symmetrically about a center-line of the front portion of the helmet.

4. The protective helmet of claim 1, wherein the moisture absorbent extension tab comprises a moisture wicking material adapted to draw moisture away from the forehead pad to the moisture absorbent extension tab.

5. The protective helmet of claim 1, wherein the fastener removably couples the moisture absorbent extension tab to the rim.

6. A protective helmet, comprising:
an energy management material comprising an outer surface and an inner surface facing away from the outer surface, and a rim positioned between the inner surface and the outer surface;
a fit system coupled to the energy management material and positioned inside the helmet;
a pad assembly coupled to the fit system, the pad assembly comprising:
a moisture absorbent forehead pad positioned in a front portion of the helmet proximate the rim;
one or more pad fingers extending from the moisture absorbent forehead pad toward a rear end of the protective helmet; and
at least one moisture absorbent extension tab extending from the forehead pad and across a portion of a surface of the rim outward of the inner surface of the energy management material.

7. The protective helmet of claim 6, further comprising a fastener positioned between the at least one moisture absorbent extension tab and the rim and coupling the moisture absorbent extension tab to the rim.

8. The protective helmet of claim 6, wherein the at least one moisture absorbent extension tab extends across more than half a width of the rim between the inner surface and the outer surface.

9. The protective helmet of claim 8, wherein the at least one moisture absorbent extension tab extends across at least ¾ of the width of the rim between the inner surface and the outer surface.

10. The protective helmet of claim 6, wherein the at least one moisture absorbent extension tab couples to the rim at the front portion of the helmet configured to be positioned above a nose of a wearer of the helmet.

11. The protective helmet of claim 6, wherein the at least one moisture absorbent extension tab couples to the rim at a front half of the helmet.

12. The protective helmet of claim 6, wherein the at least one moisture absorbent extension tab is positioned on the surface of the rim symmetrically about a center-line of the front portion of the helmet.

13. The protective helmet of claim 6, wherein the pad assembly removably couples to the energy management material.

14. A protective helmet, comprising:
a shell assembly comprising an outer surface and an inner surface facing away from the outer surface, and a rim positioned between the inner surface and the outer surface of the shell assembly; and
a pad assembly coupled to the helmet inside of the shell assembly, the pad assembly comprising:
a moisture absorbent forehead pad positioned in a front portion of the helmet proximate the rim;
one or more pad fingers extending from the moisture absorbent forehead pad toward a rear end of the protective helmet; and
at least one moisture absorbent extension tab coupled to the forehead pad and extending across a portion of a surface of the rim outward of the inner surface of the shell assembly.

15. The protective helmet of claim 14, further comprising a fastener positioned between the moisture absorbent extension tab and the rim and coupling the moisture absorbent extension tab to the rim.

16. The protective helmet of claim 14, wherein the shell assembly further comprises:
an outer shell, wherein the outer surface of the shell assembly is an outer surface of the outer shell; and
an energy management material positioned within the outer shell, wherein the inner surface of the shell assembly is an inner surface of the energy management material facing away from the outer shell.

17. The protective helmet of claim 16, wherein the at least one moisture absorbent extension tab extends across at least ¾ of a distance across the rim between the inner surface and the outer surface, and wherein the at least one moisture absorbent extension tab couples to the rim at the front portion of the helmet positioned symmetrically about a center of the helmet.

18. The protective helmet of claim 14, further comprising a recess in the surface of the rim, wherein a fastener removably couples the moisture absorbent extension tab to the rim at the recess.

19. The protective helmet of claim 18, wherein the moisture absorbent extension tab does not protrude beyond a depth of the recess for more than half of a height of the moisture absorbent extension tab.

20. The protective helmet of claim 14, wherein the moisture absorbent extension tab further comprises a plurality of channels on a surface of the moisture absorbent extension tab and extending outward from the forehead pad.

* * * * *